United States Patent
Nagale et al.

(10) Patent No.: US 10,827,939 B2
(45) Date of Patent: Nov. 10, 2020

(54) STEERABLE TISSUE MAPPING AND ABLATION DEVICE

(71) Applicant: Boston Scientific Scimed, Inc., Maple Grove, MN (US)

(72) Inventors: Sandra Nagale, Bolton, MA (US); Bryan Clark, Forest Lake, MN (US); Allan Shuros, St. Paul, MN (US); Ding He, Tyngsboro, MA (US); Dennis Werner, St. Paul, MN (US); Lynne Swanson, Edina, MN (US); Charles Gibson, Malden, MA (US); Amedeo Chiavetta, Derry, NH (US); Michael Peterson, Newburyport, MA (US); Shibaji Shome, Arden Hills, MN (US); Mark Boden, Harrisville, RI (US); Timothy Harrah, Cambridge, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 299 days.

(21) Appl. No.: 15/227,758

(22) Filed: Aug. 3, 2016

(65) Prior Publication Data
US 2017/0035497 A1    Feb. 9, 2017

Related U.S. Application Data

(60) Provisional application No. 62/200,326, filed on Aug. 3, 2015.

(51) Int. Cl.
*A61B 5/042* (2006.01)
*A61B 18/14* (2006.01)
(Continued)

(52) U.S. Cl.
CPC ........ *A61B 5/0422* (2013.01); *A61B 18/1492* (2013.01); *A61B 2017/00022* (2013.01); *A61B 2017/00044* (2013.01); *A61B 2017/00053* (2013.01); *A61B 2018/0022* (2013.01); *A61B 2018/00255* (2013.01); *A61B 2018/00267* (2013.01); *A61B 2018/00517* (2013.01); *A61B 2018/00577* (2013.01);
(Continued)

(58) Field of Classification Search
CPC .......................... A61B 5/0422; A61B 18/1492
See application file for complete search history.

(56) References Cited

U.S. PATENT DOCUMENTS 5,345,936 A * 9/1994 Pomeranz ............ A61B 5/0422
                                                          600/374
5,702,438 A * 12/1997 Avitall ............... A61B 18/1492
                                                          600/374
(Continued)

FOREIGN PATENT DOCUMENTS

CN    103417290 A    12/2013
JP    2002542891 A   12/2002
(Continued)

*Primary Examiner* — Lee S Cohen (57) ABSTRACT

The present disclosure relates to the field of tissue mapping and ablation. Specifically, the present disclosure relates to expandable medical devices for identifying and treating local anatomical abnormalities within a body lumen. More specifically, the present disclosure relates to systems and methods of focal treatment for overactive bladders.

19 Claims, 6 Drawing Sheets

(51) Int. Cl.
*A61B 18/00* (2006.01)
*A61B 17/00* (2006.01)

(52) U.S. Cl.
CPC .............. *A61B 2018/1435* (2013.01); *A61B 2018/1467* (2013.01); *A61B 2018/1475* (2013.01)

(56) References Cited

U.S. PATENT DOCUMENTS

| | | | |
|---|---|---|---|
| 6,669,693 B2* | 12/2003 | Friedman | A61B 18/1492 606/41 |
| 6,692,490 B1* | 2/2004 | Edwards | A61B 18/1477 606/41 |
| 8,588,885 B2* | 11/2013 | Hall | A61B 5/0422 600/374 |
| 9,782,099 B2* | 10/2017 | Williams | A61B 5/6858 |
| 2002/0072738 A1 | 6/2002 | Edwards et al. | |
| 2010/0114087 A1* | 5/2010 | Edwards | A61B 8/12 606/33 |
| 2013/0211415 A1 | 8/2013 | Zerfas et al. | |
| 2014/0039356 A1 | 2/2014 | Sachs et al. | |
| 2014/0114304 A1 | 4/2014 | Wang et al. | |
| 2015/0057519 A1* | 2/2015 | Ben-David | A61B 5/6853 600/373 |
| 2015/0157402 A1 | 6/2015 | Kunis et al. | |

FOREIGN PATENT DOCUMENTS

| | | |
|---|---|---|
| JP | 2014521445 A | 8/2014 |
| JP | 2014525814 A | 10/2014 |
| JP | 2015521495 A | 7/2015 |
| JP | 2018509227 A | 4/2018 |
| WO | 2014036439 | 3/2014 |

* cited by examiner

STEERABLE TISSUE MAPPING AND ABLATION DEVICE

CROSS-REFERENCE TO RELATED APPLICATIONS

This application claims priority to U.S. Provisional Application Ser. No. 62/200,326, filed on Aug. 3, 2015, the entire disclosure of which is herein incorporated by reference.

FIELD

The present disclosure relates to the field of tissue mapping and ablation. In particular, the present disclosure relates to devices and methods for proper positioning of mapping and ablation electrodes within body lumens, including the bladder.

BACKGROUND

Overactive bladder is a medical condition that affects more than 50 million people in the United States. Individuals with an overactive bladder typically experience an increase in urge and frequency of urination, and occasionally incontinence. An overactive bladder may result from increased triggering of the sensory pathways involved in normal bladder control. It has been suggested that abnormal bladder activity may result from morphological changes in one or more distinct anatomical areas of the bladder, including the dome, internal sphincter or trigone. For example, localized changes in detrusor muscle morphology resulting from defects at the cellular and multicellular level tend to correlate with pathological changes, e.g., patchy denervation due to increased amounts of connective tissue between muscle bundles, which may contribute to abnormal muscle function on a macroscopic level. These localized defects often manifest as elevated electrical activity within specific tissue regions of the bladder wall. Identifying and treating these localized defects may prevent or eliminate the symptoms of overactive bladder. Current treatments for overactive bladder, such as systemic administration of drugs, nerve stimulation or Botox injections, are applied to the entire bladder rather than specifically targeting local anatomical abnormalities. Because the therapeutic effect eventually wears off, these treatments often need to be repeated multiple times. Unfortunately, overtreatment may lead to urinary retention that requires self-catheterization to void the bladder.

The transient nature of these systemic treatments may be addressed by mapping the tissues of the bladder wall to identify where local bladder abnormalities originate and then specifically targeting therapeutic treatment to those areas. Currently available bladder mapping devices do not conform to the shape of the bladder and cannot reliably establish and/or maintain contact between each of the electrodes and the bladder wall. Proper positioning of the electrodes may be achieved by, for example, placing the electrodes on an expandable framework or attaching the electrodes to the surface of a balloon, as described by Drake et al. (BJU International 2005, vol. 95, pp. 1002-1005). Due to the asymmetric nature of the bladder, it is important that the device be properly oriented prior to expansion. However, conventional catheters simply deliver these devices into the central lumen of the bladder regardless of the specific internal dimensions. This often prevents the mapping and ablation electrodes from contacting a significant portion of the bladder wall.

There is a continued need for mapping and ablation systems that conform to the shape of an individual's bladder, along with a steerable delivery system that allows for precise orientation prior to deployment.

SUMMARY

Particular embodiments of the disclosure are described in the Summary and Detailed Description of the Preferred Embodiments, below. Although the disclosure has been described in connection with specific embodiments, it should be understood that the disclosure as claimed should not be unduly limited to such specific embodiments.

The present disclosure relates generally to electrode-bearing mapping and ablation systems that provide enhanced electrical connection with the bladder wall. In one aspect, the present disclosure relates to a medical device, comprising a steerable catheter comprising a proximal end, a distal end and a lumen extending therebetween; an expandable-collapsible framework slidably disposed within the lumen of the steerable catheter; and a plurality of electrodes carried about a surface of the expandable-collapsible framework. The expandable-collapsible framework may be formed from a shape memory material that assumes a pre-determined shape when not disposed within the lumen of the steerable catheter. Each of the plurality electrodes may be configured to serve as a sensing electrode, mapping electrode, stimulating electrode and/or ablation electrode. Each of the plurality of electrodes may contact a wall of the body lumen when the framework is in an expanded configuration. The expandable-collapsible framework may substantially maintain its shape (on a geometrically similar basis) as it is pushed from the catheter and expands. The expandable-collapsible framework may curve relative to a longitudinal axis of the medical device when in an expanded state. The expandable-collapsible framework may comprise a plurality of longitudinal members formed from a shape memory material that assumes a curved shape. The flexibility of each longitudinal member may vary along its length. Each of the longitudinal members may be joined together at their distal ends. A plurality of cross-pieces may extend between each of the curved longitudinal members. In addition or alternatively, the expandable-collapsible framework may include an internal support to bias the longitudinal members outward. The internal support may include an additional expandable framework or an inflatable balloon. The expandable-collapsible framework may further include a plurality of conducting wires such that a first end of each conducting wire is electrically coupled to a different one of the plurality of electrodes and a second end of each conducting wire is optionally electrically coupled to an ablation energy source and/or an electrical activity processing system. The ablation energy source may include a radio frequency (RF) generator. The electrical activity processing system may be configured to measure intrinsic electrical activity.

In another aspect, the present disclosure relates to a medical device, comprising: a catheter comprising a proximal end, a distal end and a lumen extending therebetween; a helically-biased wire comprising a proximal end and a distal end slidably disposed within the lumen of the steerable catheter; and a plurality of electrodes carried about a surface of the helically-biased wire. Each of the plurality electrodes may be configured to serve as a sensing electrode, mapping electrode, stimulating electrode and/or ablation electrode. The helically-biased wire may be formed from a shape memory material that assumes a pre-determined shape when not disposed within the lumen of the steerable catheter. A diameter of the helically-biased wire may increase from the distal end toward a center of the helically-biased wire and from the proximal end toward the center of the helically-biased wire. An elongate member may be disposed within the catheter such that a distal end of the elongate member is attached to the distal end of the helically-biased wire. Each of the plurality of electrodes may contact a wall of the body lumen when the helically-biased wire is in an expanded configuration. The medical device may further include a plurality of conducting wires, wherein a first end of each of the conducting wires is electrically coupled to a different one of the plurality of electrodes, and a second end of each of the conducting wires is electrically coupled to an ablation energy source and/or an electrical activity processing system. The ablation energy source may include a radio frequency (RF) generator. The electrical activity processing system may be configured to measure intrinsic electrical activity.

In another aspect, the present disclosure relates to a method comprising: introducing a medical device into a body lumen, wherein the medical device includes a steerable catheter comprising: a proximal end, a distal end and a lumen extending therebetween; an expandable-collapsible framework slidably disposed within the lumen of the steerable catheter; and a plurality of electrodes carried about a surface of the expandable-collapsible framework; moving the framework to an expanded configuration such that the electrodes carried about the surface of the framework contact a tissue of the body lumen; measuring the electrical activity within the tissue of the body lumen in contact with each of the electrodes; identifying each electrode that detected an elevated electrical activity within the tissue of the body lumen; and applying electrical energy to each electrode that identified elevated electrical activity. The body lumen may include the lumen of a bladder. The electrical energy applied by each electrode may reduce the elevated electrical within the tissue of the body lumen, thereby reducing at least one symptom of an overactive bladder.

In another aspect, the present disclosure relates to a method comprising: introducing a medical device into a body lumen, wherein the medical device includes a catheter comprising a proximal end, a distal end and a lumen extending therebetween; a helically-biased wire comprising a proximal end and a distal end slidably disposed within the lumen of the steerable catheter; and a plurality of electrodes carried about a surface of the helically-biased wire; moving at least a portion of the helically-biased wire beyond the distal end of the catheter such that the helically-biased wire expands and the electrodes carried about the surface of the helically-biased wire contact a tissue of the body lumen; measuring the electrical activity within the tissue of the body lumen in contact with each of the electrodes; identifying each electrode that detected an elevated electrical activity within the tissue of the body lumen; and applying electrical energy to each electrode that identified elevated electrical activity. The body lumen may include the lumen of a bladder. The electrical energy applied by each electrode may reduce the elevated electrical within the tissue of the body lumen, thereby reducing at least one symptom of an overactive bladder.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of ordinary skill in the art to understand the disclosure. In the figures.

DETAILED DESCRIPTION OF THE PREFERRED EMBODIMENTS

Before the present disclosure is described in further detail, it is to be understood that the disclosure is not limited to the particular embodiments described, as such may vary. It is also to be understood that the terminology used herein is for the purpose of describing particular embodiments only, and is not intended to be limiting beyond the scope of the appended claims. Unless defined otherwise, all technical terms used herein have the same meaning as commonly understood by one of ordinary skill in the art to which the disclosure belongs. Finally, although embodiments of the present disclosure are described with specific reference to systems and methods for mapping and ablating overactive tissue(s) within the bladder, it should be appreciated that the present disclosure may be applicable to mapping and ablating a variety of organs, including, for example, the gastrointestinal (GI) tract, stomach (e.g., irritable bowel disease, cancer, obesity etc.), uterus (e.g., fibroids, uterine bleeding etc.), esophagus, heart and vascular system.

As used herein, the term "distal" refers to the end farthest away from a medical professional when introducing a device into a patient, while the term "proximal" refers to the end closest to the medical professional when introducing a device into a patient.

As used herein, "expandable" or "expanded" refers to an increase in diameter, as compared to the diameter in a "collapsible" or "collapsed" configuration. As used herein, "diameter" refers to the distance of a straight line extending between two points and does not necessarily indicate a particular shape.

All of the devices and/or methods disclosed and claimed herein can be made and executed without undue experimentation in light of the present disclosure. While the devices and methods of this disclosure have been described in terms of preferred embodiments, it will be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

Figure 1:
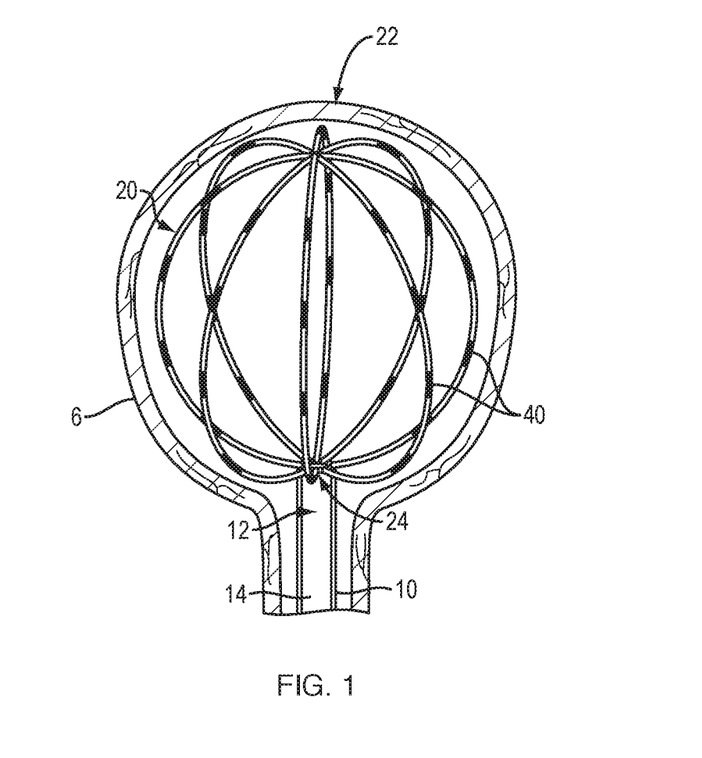
FIG. 1 is a schematic side view of a mapping and ablation system comprising an expandable-collapsible framework that includes a proximal end and a distal end, between which flexible splines extend in a circumferentially spaced relationship, according to an embodiment of the present disclosure.
Figure 2:
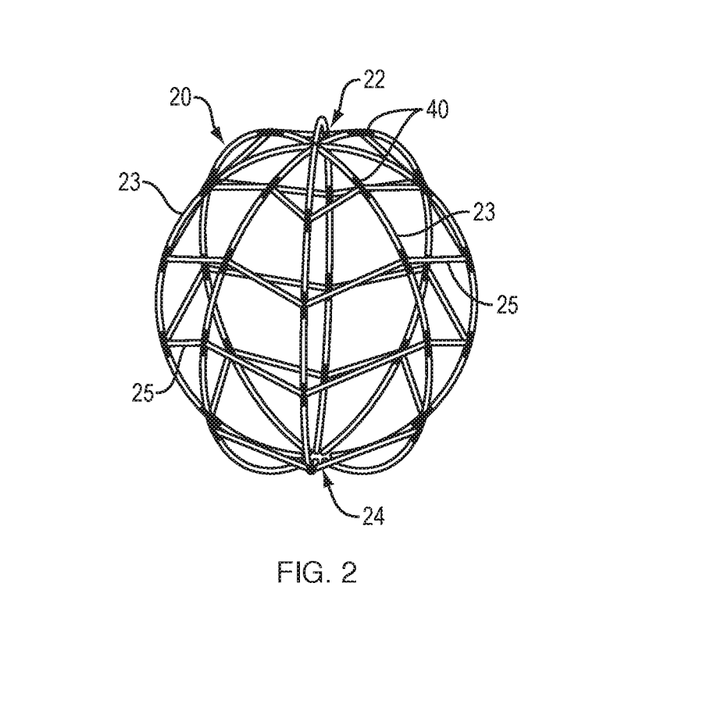
FIG. 2 is a schematic side view of the framework of FIG. 1, wherein adjacent splines are connected by one or more cross-pieces to form a lattice-like structure, according to another embodiment of the present disclosure.

FIG. 1 provides a schematic side view of a medical device comprising a catheter 10 that includes a proximal end (not shown), distal end 12 and lumen 14 extending therebetween. An expandable-collapsible framework 20 is slidably disposed within the lumen 14 of the catheter 10. The framework 20 includes a proximal end 24 and a distal end 22, between which a plurality of flexible curved longitudinal members (i.e., flexible splines 23) extend in a circumferentially spaced relationship. In some embodiments, the splines 23 that form the framework may include regions of varying flexibility and/or stiffness such that the framework 20 conforms to bladders of various shapes and sizes when in the expanded configuration. As shown in FIG. 2, adjacent splines 23 may be connected by a series of cross-pieces (i.e., struts 25) to form a mesh- or basket-like structure with enhanced structural integrity that defines an interior space when in the expanded configuration. The splines 23 and struts 25 may be made, for example, from a resilient inert material, including metals and metal alloys such as platinum, tungsten, titanium, stainless steel, nickel and nickel-titanium alloys (e.g., nitinol), polymers such as acrylate-based polymers, polyurethane-based polymers, polynorbornene-based polymers, and polylactide-based polymers, and any combinations thereof.

A plurality of unipolar or bipolar electrodes 40 may be connected equidistantly about the outer surface of the framework 20 to identify and ablate tissue regions of the bladder wall 6 that exhibit aberrant electrical activity. In one particular embodiment (e.g., FIG. 2), an electrode may be attached at the intersection of each spline and strut. Each electrode may be electrically coupled to an electrical activity processing system and an ablation energy source by a separate electrically conductive wire that extends along the inner or outer surface of the framework (not shown). In another embodiment, the electrodes may be electrically coupled to an electrical activity processing system and ablation energy source by one or more flexible circuits printed along the inner or outer surface of the splines and/or struts of the framework. In yet another embodiment, the flexible printed circuits may form the splines and/or struts of the framework.

Figure 3:
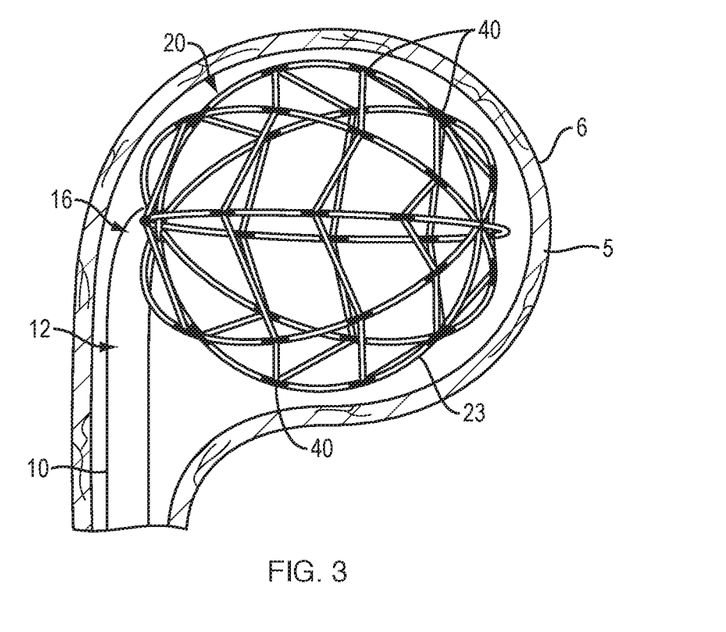
FIG. 3 is a schematic side view of a mapping and ablation system comprising an expandable-collapsible framework that is deployable from the lumen of a steerable catheter, according to another embodiment of the present disclosure.

As best illustrated in FIG. 3, in some embodiments, the distal end 12 of the catheter 10 may include a steerable segment 16 comprising a flexible and/or bendable material. Examples of steerable catheters may be found, for example, in U.S. Pat. Nos. 5,656,030 and 6,837,867 and U.S. Patent Publication No. 20100010437, which are hereby incorporated by reference. The steerable segment 16 allows the framework 20 to be precisely positioned within the bladder 5 to ensure that the splines 23 are in direct apposition with the bladder wall 6. For example, the framework 20 may be delivered into a symmetrically shaped (e.g., spherical) bladder by positioning the catheter such that the distal end points toward the top of the bladder wall. As the framework exits the catheter lumen 14, it will expand in a substantially uniform manner to fill the bladder. If, however, the bladder is asymmetrically shaped, e.g., the bladder is offset to one side, the catheter 10 may be oriented (i.e., steered) such that the distal end 12 preferentially points toward the predominant portion of the bladder. The ability to steer the distal end 12 of the catheter 10 allows the user to deliver the framework 20 within an asymmetrically shaped bladder in a manner that provides improved apposition of the splines 23 against the bladder wall 6.

Figure 4:
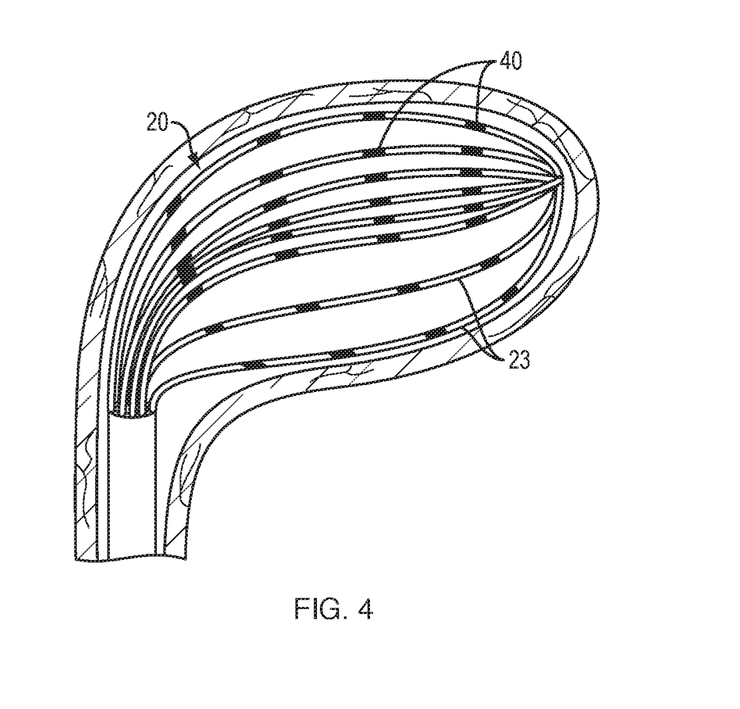
FIG. 4 is a schematic side view of a mapping and ablation system that includes a framework formed from a series of offset splines for deployment within an asymmetrically shaped body lumen, according to another embodiment of the present disclosure.

As illustrated in FIG. 4, the splines 23 of the framework 20 may also be preferentially offset to one side to accommodate deployment within an asymmetrically shaped lumen. In one embodiment, each of the splines 23 may be individually deployed and/or retracted through the catheter lumen 14 as necessary to ensure that each spline conforms to the specific dimensions of the bladder wall. In addition, or alternatively, the interior space of the framework may include an asymmetric expander (not shown) configured to preferentially push the framework in one direction.

Figure 5A:
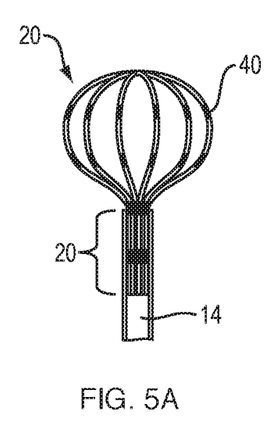
FIG. 5A, FIG. 5B and FIG. 5C depict the spherical shape of an expandable-collapsible framework as it exits the distal tip of the steerable catheter, according to another embodiment of the present disclosure.
Figure 5B:
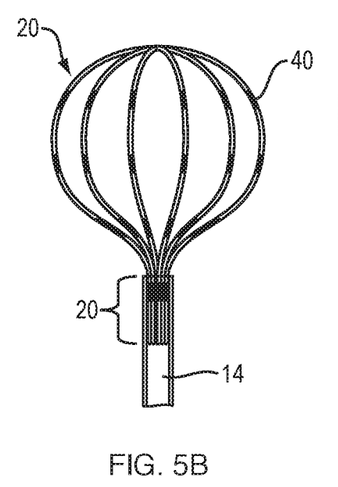
Figure 5C:
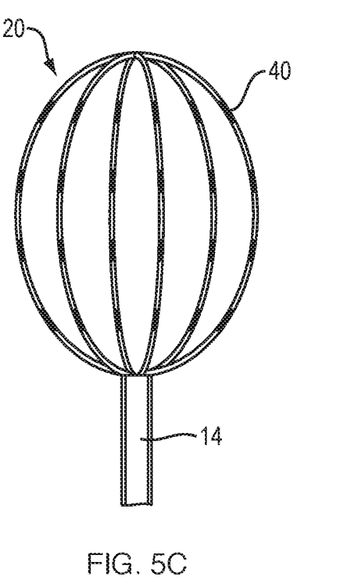

As will be understood by those of skill in the art, the shape memory material comprising the framework may form any number of three-dimensional expanded shapes. In one embodiment, the pre-determined expanded shape may begin to form as the framework exits the lumen of the catheter, without necessarily requiring complete deployment. For example, as illustrated in FIGS. 5A-5C, a framework 20 that includes a substantially spherical expanded shape may assume that shape as it is being deployed, independent of how much of the framework remains within the catheter lumen 14. This allows the framework to be deployed incrementally as dictated by the size and/or shape of the bladder to ensure that each spline conforms to the specific dimensions of the bladder wall.

Figure 6:
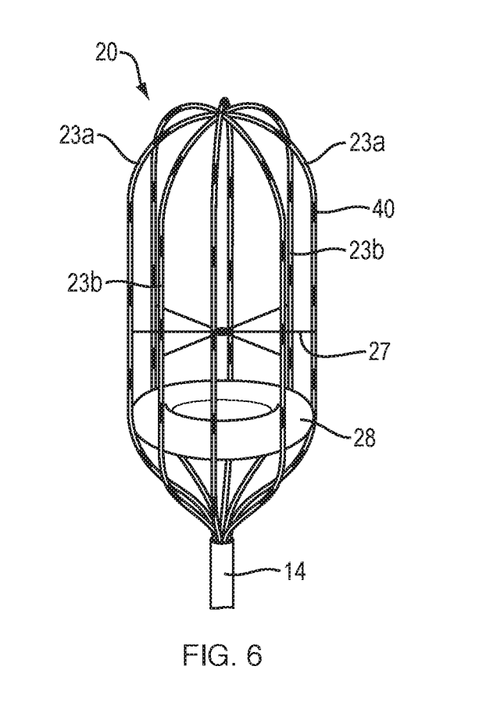
FIG. 6 is a schematic side view of an expandable-collapsible framework that includes a relatively rigid dome and semi-flexible splines, according to another embodiment of the present disclosure.

Referring to FIG. 6, the ability of the framework 20 to conform to the bladder may be further adjusted by varying the flexibility of the splines 23 depending on their location within the framework. For example, the portion of each spline comprising the curved dome 23a of the framework may be formed from a relatively rigid (i.e., stiff) shape memory material that resists deformation as it compresses against the bladder wall. The longitudinal portion of each spline 23b connected to the rigid dome may be formed from a shape memory material that is more flexible than the relatively rigid shape memory material, for example, a semi-flexible (i.e., pliable) shape memory material that can bend inward or bow outward according to the corresponding contour of the bladder wall. Once properly positioned, an expansion piece 27 located within a middle portion of framework 20 may be used to urge the longitudinal portion of each spline 23*b* outward against the bladder wall. The expansion piece may maintain the splines in their proper location and provide internal support to prevent the splines from collapsing. A telescoping element (not shown) may be connected to a center portion of the expansion piece 27. The telescoping element may extend through the lumen of the catheter to advance and/or retract the expansion piece 27 within the framework as necessary to properly support the framework 20 and, once properly positioned, to lock the expansion piece in place. The telescoping element may be retracted distally to allow the framework to collapse for removal. An expandable balloon 28 (or balloons) may also be positioned within the framework 20. The balloon may be inflated as necessary to urge the splines 23 outward against the bladder wall and maintain the framework in the desired expanded configuration. The balloon may then be deflated to allow the framework to collapse for removal. In the embodiment shown, the balloon 28 is provided proximate to the region where the splines taper into the catheter lumen 14, but could also be provided anywhere within the framework. In the embodiment shown, the balloon 28 is of annular (donut) shape, but could also be provided in a number of other shapes including spheroidal (e.g., in the form of a sphere, oblate spheroid or prolate spheroid), among others.

Figure 7A:
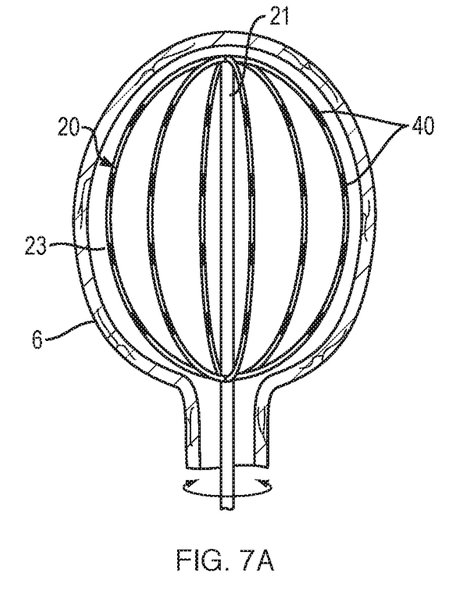
FIG. 7A and FIG. 7B provide a schematic side view of an expandable-collapsible framework that includes a central telescoping arm that may be rotated about its axis to force the splines of the framework to move into a twisted configuration, according to another embodiment of the present disclosure.
Figure 7B:
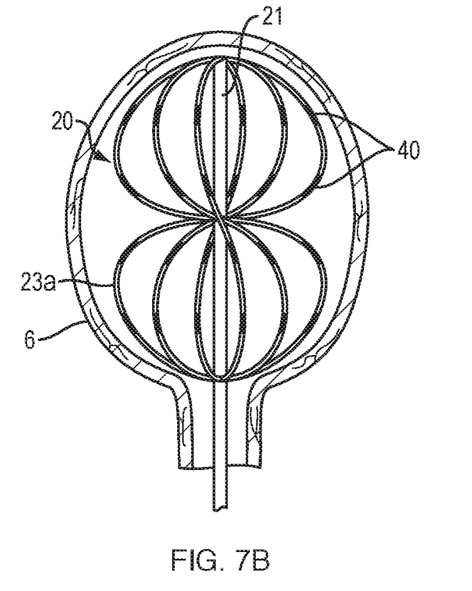

Referring to FIGS. 7A-7B, the ability to adjust the splines 23 to conform to the bladder wall 6 may be further enhanced with a central telescoping arm 21 that extends through the lumen of the catheter and the center of the framework 20. The distal end of each spline 23 is attached to the distal end of the telescoping arm 21 and the proximal end of each spline 23 is free-floating about a middle portion of the telescoping arm 21. As shown in FIG. 7A, each of the splines aligns with the axis of the central telescoping arm in a substantially linear configuration. As shown in FIG. 7B, rotating the proximal end (not shown) of the central telescoping 21 arm exerts tension (i.e., torque) along the length of each spline 23, forcing the splines into a twisted configuration 23*a* about the axis of the telescoping arm. The relative stiffness of each spline increases as it moves from the straight to twisted configuration 23*a*, thereby placing each spline in firm apposition with the bladder wall 6.

Figure 8A:
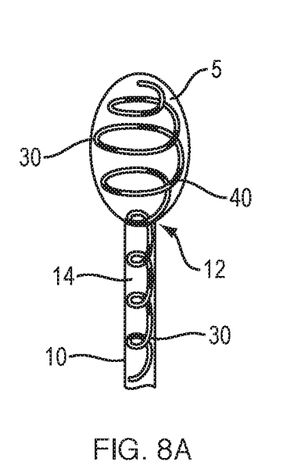
FIG. 8A, FIG. 8B and FIG. 8C each provide a schematic side view of a mapping and ablation system that includes a shape memory wire with a helical bias that is deployable from the lumen of a steerable catheter, according to another embodiment of the present disclosure.
Figure 8B:
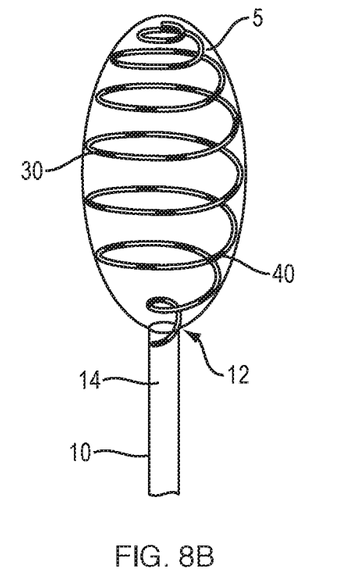
Figure 8C:
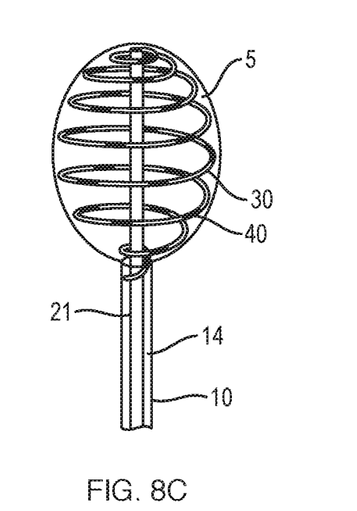

Referring to FIGS. 8A-8C, the framework of FIGS. 1-7 may be replaced with a wire 30 formed from a shape memory material that includes a helical bias. A plurality of electrodes may be disposed along the length of the wire. In one embodiment, the wire 30 may be formed from a plurality of separate wires, each of which is electrically connected to a different one of the plurality of electrodes. As best illustrated in FIG. 8A, the wire may be formed as a tight spiral coil when disposed within the lumen 14 of the catheter 10. As the wire exits the distal end 12 of the catheter at or near the top (i.e., dome) of the bladder 5, the helical bias urges the unconstrained wire 30 into a series of coils that expand according to the shape of the bladder. In another embodiment (not shown), the wire may be formed as a tight spiral coil wrapped around a stylet (i.e., guidewire) slidably disposed within the lumen of the catheter. The stylet and wire may be advanced through the lumen of the catheter into the bladder. Once properly positioned within the bladder, the stylet may be withdrawn from the tight spiral coil. As above, the helical bias urges the unconstrained wire into a series of coils that expand according to the shape of the bladder. More or less of the wire may 30 be advanced through the lumen 14 of the catheter 10 depending of the size of the bladder. For example, only a portion of the wire 30 is required to fill the smaller bladder 5 of FIG. 8A, while the entire wire 30 is required to fill the larger bladder 5 of FIG. 8B. As shown in FIG. 8C, the coils of the helically-biased wire 30 may be adjusted to conform to the bladder wall by a central telescoping arm 21 that extends through the lumen 14 of the catheter 10 and is connected to the distal end of the helically-biased wire 30. In one embodiment, retracting the proximal end (not shown) of the central telescoping 21 arm longitudinally compresses and urges coils of the helically-biased wire 30 to move radially outward against the bladder wall. Alternatively, the proximal end of the central telescoping arm 21 may be rotated in the direction of the winding of the helically-biased wire 30 to partially "wind" the helically-biased wire 30 or, conversely, rotated in a direction counter to the direction of winding of the wire 30 to partially "unwind" the helically-biased wire 30. This "unwinding" releases a portion of the tension on the helically-biased wire 30 such that the winding of the helically-biased wire 30 expands in diameter, placing the helically-biased wire 30 into contact with the bladder wall.

Figure 9A:
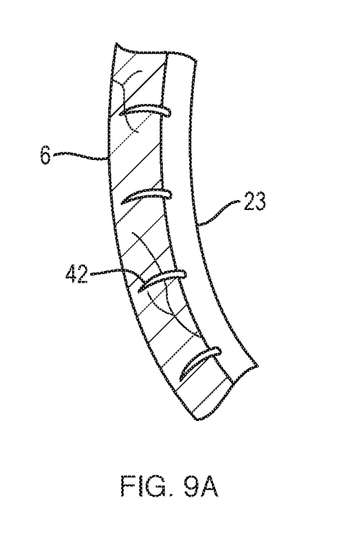
FIG. 9A and FIG. 9B depict a plurality of retractable needle electrodes extending from a spline of the mapping and ablation system into the bladder wall, according to another embodiment of the present disclosure.
Figure 9B:
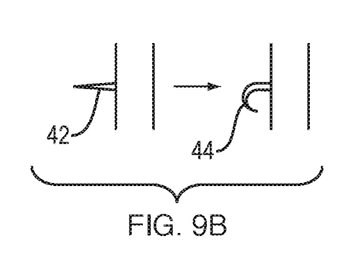

The surface of the framework or helically-biased wires described herein may include a variety of electrodes configured to "self-position" within the creases of the bladder wall. For example, as shown in FIG. 9A-9B, a plurality of needle-shaped electrodes 42 (i.e., tines) may be disposed about the outer surface of each spline 23 to anchor the splines to the bladder wall 6. These tines may be linear or non-linear, for example, formed into the shape of a hook 44 to further secure each electrode to the bladder wall. The increased adhesion offered by these tines may reduce noise artifacts common to mapping procedures, thereby allowing more accurate and reliable mapping of the bladder wall and more accurate focal delivery of ablation energy. The tines may be retractable to allow the framework or helically-biased wire to be released from the bladder wall without causing tissue damage once the mapping and ablation procedure is completed. The tines may further include one or more channels (not shown) for selectively delivering therapeutic agents, including, by way of non-limiting example, Botox or a neurotoxin into the bladder wall.

Figure 10A:
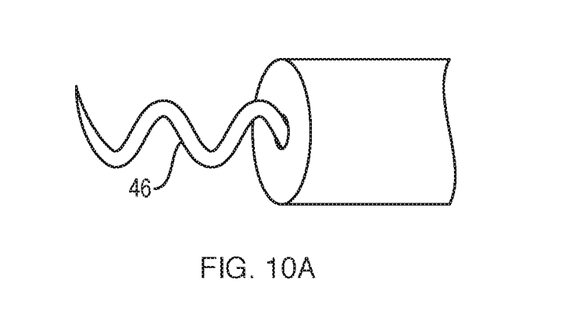
FIG. 10A and FIG. 10B depict alternative electrode configurations, according to additional embodiments of the present disclosure.
Figure 10B:
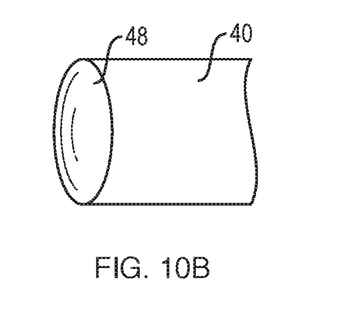
Figure 11A:
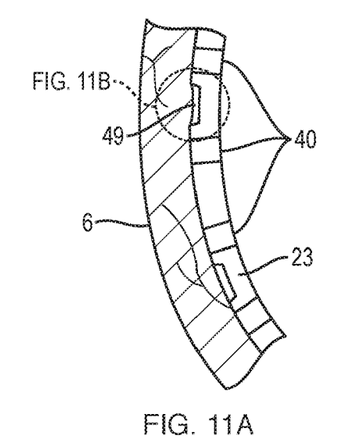
FIG. 11A, FIG. 11B and FIG. 11C depict a section of the expandable-collapsible framework that includes a series of openings through which a suction may be applied to secure the framework to the bladder wall, according to another embodiment of the present disclosure.
Figure 11B:
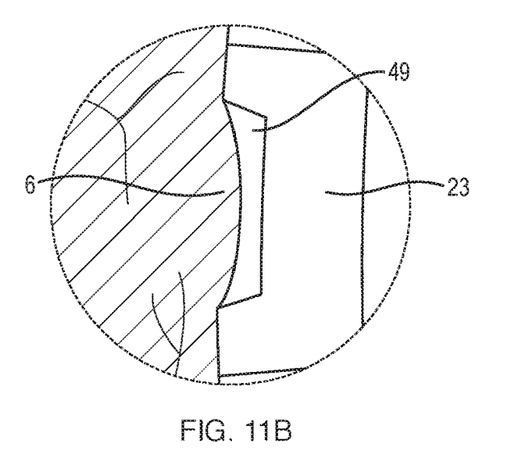
Figure 11C:
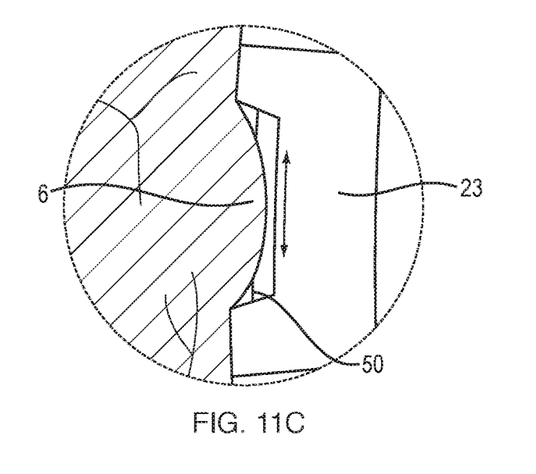

As shown in FIG. 10A, the electrode tines may include a helical shape 46 that serves as a "cork-screw" to penetrate the bladder wall. As an alternative to actively penetrating the bladder wall, the end of each electrode may include a channel 48 through which negative pressure (i.e., suction) may be drawn to temporarily secure the electrode 40 to the bladder wall (FIG. 10B). Alternatively, as shown in FIGS. 11A-11B, a section of each spline 23 may include a series of openings 49 through which negative pressure may be drawn, thereby placing the electrodes 40 adjacent to each opening 49 in contact with the bladder wall 6. Referring to FIG. 11C, in some embodiments, once the tissues of the bladder wall 6 are drawn into the openings 40, a slidable pin 50 may be advanced across the opening 49 (see arrows) into or through the tissue, thereby holding the tissue in place, in which case the pin 50 may also serve dual propose as an electrode.

In additional aspects, the framework splines and/or helically-biased wire of the present disclosure may include color-coded markings for visualization (e.g., using a cystoscope) to allow the physician to verify that the electrodes are properly positioned within the bladder prior to initiating the mapping and/or ablation steps. In addition, or alternatively, the framework splines and/or helically-biased wire may incorporate radiopaque markers along their length to allow the physician to verify their position within the bladder using, for example, X-ray imaging. In yet another embodiment, proper positioning of each electrode in apposition with the bladder wall may be achieved by measuring the impedance at each electrode. Any electrode(s) that fail to provide an impedance reading indicative of contact with the bladder wall may be re-positioned accordingly. In the event that one or more electrodes cannot be appropriately positioned in apposition with the bladder wall, any electrical measurements received from such electrodes may be disregarded during the mapping procedure.

In other aspects, proper alignment of the mapping and ablation system of the present disclosure may be achieved using an insertion device that includes, for example, a shaft with a non-circular lumen configured to receive the mapping and ablation system in a specific orientation. The insertion device may include a guide (i.e., notch) to ensure that the mapping and ablation system is properly aligned with the non-circular lumen during loading. The insertion device may further include markings that correspond to the position of the patient, e.g., "ventral," "dorsal," "left," and "right" to further ensure proper insertion into the patient's bladder. A series of incremental markings may also be included along the length of the insertion device to allow the physician to monitor how far within the patient the device has been inserted. The non-circular lumen of the insertion device may further allow the mapping and ablation system to automatically return (e.g., spring back) to the proper orientation if it becomes misaligned during insertion into the patient.

In other aspects, the steerable catheter of the presently disclosed mapping and ablation system may include a central lumen through which a variety of medical instruments may be introduced. One such central lumen is shown as lumen 14 in FIG. 1. For example, an optical scope may be inserted through this central lumen to allow the physician to visually verify the location of the device within the bladder. Additional catheters may also be inserted through this central lumen to deliver fluids to keep the bladder wall hydrated and/or to expand the bladder to various volumes. Such fluids may also include therapeutics agents, or serve to cool the bladder during the ablation process.

Examples of mapping electrode for use with medical ablation systems may be found, for example, in U.S. Patent Publication Nos. 2008/0249518 and 2002/0177765, each of which are hereby incorporated by reference in their entirety. As mapping electrodes, the wire connected to each electrode may be electrically coupled to the input of an electrical activity processing system (not shown), such as, for example, an electromyograph. Each electrode may be assigned an electrode location and an electrode channel within the electrical activity processing system. The electrical activity processing system may be configured to detect the intrinsic electrical activity of the cells comprising the tissue region that each of the electrodes is in contact with. The electrical activity processing system may then use the intrinsic electrical activity detected from each of the electrodes to provide a map of electrical activity and signal propagation throughout a given tissue region or organ. Based on this map, specific tissue regions exhibiting aberrant electrical activity as compared to the surrounding tissues may be identified. For example, the aberrant electrical activity may manifest as a region of elevated electrical activity compared to the surrounding (normal) tissue.

For use as ablation electrodes, each wire may also be electrically coupled to an energy source (not shown) configured to selectively deliver ablation energy its respective electrode. For example, once a tissue region exhibiting elevated electrical activity has been identified, the electrode(s) that detected the elevated electrical activity may be selectively energized to focally ablate that tissue region. Various energy sources may be used to deliver thermal energy to the target tissue, including, for example, radiofrequency (RF) energy, irreversible electroporation (IRE energy), microwave electromagnetic energy, laser energy, and/or acoustic energy, among others. For example, the energy source may include a conventional RF power supply that operates at a frequency in the range from 200 KHz to 1.25 MHz, with a conventional sinusoidal or non-sinusoidal wave form. Suitable power supplies are capable of supplying an ablation current at a relatively low voltage, typically below 150V (peak-to-peak), usually being from 50V to 100V. It should be appreciated that a variety of RF energy generators that provide impedance, electrode temperature measurement and adequate energy output may be used to achieve appropriate ablation of the bladder tissue. RF energy may be delivered via a simultaneous mode with a single RF generator or multiple RF generators. Simultaneous delivery of ablation energy to 64 electrodes will require a generator capable of delivering approximately 640 W. This wattage may be achieved by connecting multiple generators, e.g., 64 generators with a capacity of 20 W in series. Power supplies capable of operating within these ranges are available from commercial vendors, such as RadioTherapeutics of San Jose, Calif.

Once any one of medical devices disclosed herein are properly positioned within the bladder, the mapping function of each electrode may be activated to sense/detect the intrinsic electrical activity of the tissue region they are in contact with. Once a tissue region of the bladder wall exhibiting elevated electrical activity has been identified, ablation energy may be selectively delivered from the energy source to the electrode(s) that sensed the elevated electrical activity. This focal delivery of ablation energy causes the electrically overactive cell(s) of the identified tissue region to be heated to the point of cell death, thereby creating scar tissue that is incapable of conducting electrical impulses.

The duration and/or intensity of the ablation energy may vary as necessary to achieve a satisfactory reduction of the elevated electrical activity. For example, ablation energy may be provided as a pulse, or series of pulses, of RF energy. The mapping function of the electrodes may then be re-established to determine if the identified tissue region continues to exhibit elevated electrical activity. In the event that the electrical activity within such sites remains elevated, the selected tissue region may be re-energized with ablation energy. This process may be repeated as necessary until the tissue region exhibits a desired level of electrical activity. The ability of these electrode arrays to repeatedly monitor and ablate regions of the bladder wall ensures that focal energy is delivered only to the target region, and without prolonging the duration or intensity of the energy. This targeted approach not only focuses the energy on the selected regions in need of ablation, but minimizes or eliminates unwanted and potentially harmful ablation of surrounding healthy/normal tissues.

While the tissue region that is identified and ablated may be in direct contact with an electrode, it should be appreciated that the target tissue may be in the general vicinity of an electrode. In this situation, one or more of the electrodes adjacent to the target tissue may be energized such that the zone of ablation energy reaches (i.e., overlaps with) the target tissue.

Once the mapping function of the electrodes has verified that the ablated tissue region no longer exhibits elevated electrical activity, the framework or helically-biased wire may be returned to the collapsed configuration within the catheter and withdrawn through the urethra.

While the present disclosure relates generally to the application of thermal ablation energy to the target tissues identified by the mapping electrodes, it should also be appreciated the non-lethal energy, such as electrically stimulating energy or delivery of therapeutic agents through electroporation, may be administered to restore normal electrical activity to the cells of the target tissue.

What is claimed is:

1. A medical device, comprising:
a steerable catheter comprising a proximal end, a distal end and a lumen extending therebetween;
an expandable-collapsible framework slidably disposed within the lumen of the steerable catheter; and
a plurality of electrodes disposed along a length of the expandable-collapsible framework and carried equidistantly about a surface of the expandable-collapsible framework;
wherein the framework comprises a plurality of flexible curved longitudinal members with regions of varying flexibility, or varying stiffness, or both, such that the framework is configured to conform to a plurality of different sized or shaped bladders when in an expanded configuration, wherein the plurality of electrodes is configured to anchor the framework to a wall of the bladder when in the expanded configuration, and wherein the plurality of electrodes comprises a helical-shape.

2. The medical device of claim 1, wherein the expandable-collapsible framework is formed from a shape memory material that assumes a pre-determined shape when not disposed within the lumen of the steerable catheter.

3. The medical device of claim 1, wherein the expandable-collapsible framework comprises a plurality of longitudinal members formed from a shape memory material that assumes a curved shape.

4. The medical device of claim 3, further comprising an internal support for biasing the longitudinal members laterally outward.

5. The medical device of claim 4, wherein the internal support for biasing the longitudinal members laterally outward is an additional expandable framework or an inflatable balloon.

6. The medical device of claim 1, wherein each of the plurality of electrodes is configured to contact the bladder wall when the framework is in the expanded configuration.

7. The medical device of claim 1, further comprising a plurality of conducting wires, wherein a first end of each of the plurality of conducting wires is electrically coupled to a different one of the plurality of electrodes.

8. The medical device of claim 7, wherein a second end of each of the plurality of conducting wires is electrically coupled to an ablation energy source.

9. The medical device of claim 7, wherein a second end of each of the plurality of conducting wires is electrically coupled to an electrical activity processing system.

10. The medical device of claim 1, wherein each of the plurality electrodes includes a sensing electrode, a mapping electrode, a stimulating electrode or an ablation electrode, or a combination thereof.

11. A medical device, comprising:
a steerable catheter comprising a proximal end, a distal end and a lumen extending therebetween;
an expandable-collapsible framework slidably disposed within the lumen of the steerable catheter; and
a plurality of electrodes disposed along a length of the expandable-collapsible framework and carried equidistantly about a surface of the expandable-collapsible framework;
wherein the framework comprises a plurality of flexible curved longitudinal members, the flexibility of each longitudinal member varying along its length each such that the framework is configured to conform to a plurality of different sized or shaped bladders when in an expanded configuration, wherein the plurality of electrodes is configured to anchor the framework to a wall of the bladder when in the expanded configuration, and wherein the plurality of electrodes comprises a helical-shape.

12. The medical device of claim 11, wherein the expandable-collapsible framework is formed from a shape memory material that assumes a pre-determined shape when not disposed within the lumen of the steerable catheter.

13. The medical device of claim 11, wherein the expandable-collapsible framework comprises a plurality of longitudinal members formed from a shape memory material that assumes a curved shape.

14. The medical device of claim 11, wherein each of the plurality of electrodes is configured to contact the bladder wall when the framework is in the expanded configuration.

15. The medical device of claim 11, further comprising a plurality of conducting wires, wherein a first end of each of the plurality of conducting wires is electrically coupled to a different one of the plurality of electrodes.

16. The medical device of claim 15, wherein a second end of each of the plurality of conducting wires is electrically coupled to an ablation energy source.

17. The medical device of claim 15, wherein a second end of each of the plurality of conducting wires is electrically coupled to an electrical activity processing system.

18. A method, comprising:
introducing the medical device of claim 1 into a bladder;
moving the framework to an expanded configuration such that the electrodes carried about the surface of the framework contact a wall of the bladder;
measuring electrical activity within the bladder wall in contact with each of the electrodes;
identifying each electrode that detected an elevated electrical activity within the bladder wall; and
applying electrical energy to each electrode that identified elevated electrical activity.

19. The method of claim 18, wherein applying electrical energy reduces the elevated electrical activity within the bladder wall.

* * * * *